United States Patent
Tsaur et al.

(10) Patent No.: US 8,263,538 B2
(45) Date of Patent: *Sep. 11, 2012

(54) PERSONAL WASH CLEANSER WITH MILD SURFACTANT SYSTEMS COMPRISING DEFINED ALKANOYL COMPOUNDS AND DEFINED FATTY ACYL ISETHIONATE SURFACTANT PRODUCT

(75) Inventors: Liang Sheng Tsaur, Norwood, NJ (US); Kavssery P. Ananthapadmanabhan, Woodbury, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 56 days.

This patent is subject to a terminal disclaimer.

(21) Appl. No.: 12/751,049

(22) Filed: Mar. 31, 2010

(65) Prior Publication Data

US 2011/0245126 A1 Oct. 6, 2011

(51) Int. Cl.
- *A61K 8/02* (2006.01)
- *C11D 3/20* (2006.01)
- *C11D 17/00* (2006.01)
- *C11D 3/00* (2006.01)
- *C11D 7/42* (2006.01)

(52) U.S. Cl. ........ 510/159; 510/242; 510/280; 510/370; 510/393

(58) Field of Classification Search .......... 510/159, 510/242, 280, 370, 393
See application file for complete search history.

(56) References Cited

U.S. PATENT DOCUMENTS

| | | | |
|---|---|---|---|
| 3,723,325 A | 3/1973 | Parran, Jr. | |
| 4,089,945 A * | 5/1978 | Brinkman et al. | 424/702 |
| 4,554,207 A * | 11/1985 | Lee | 442/334 |
| 4,565,647 A | 1/1986 | Llenado | |
| 4,654,207 A * | 3/1987 | Preston | 510/119 |
| 5,009,814 A | 4/1991 | Kelkenberg et al. | |
| 5,132,037 A | 7/1992 | Greene et al. | |
| 5,234,619 A | 8/1993 | Greene et al. | |
| 5,290,471 A | 3/1994 | Greene et al. | |
| 5,372,751 A | 12/1994 | Rys-Cicciari et al. | |
| 5,389,279 A | 2/1995 | Au et al. | |
| 5,415,810 A | 5/1995 | Lee et al. | |
| 5,612,307 A | 3/1997 | Chambers et al. | |
| 5,703,026 A * | 12/1997 | Setser et al. | 510/152 |
| 5,716,919 A | 2/1998 | Sano | |
| 5,739,365 A | 4/1998 | Briody et al. | |
| 5,804,540 A | 9/1998 | Tsaur et al. | |
| 5,952,286 A | 9/1999 | Puvvada et al. | |
| 5,966,500 A | 10/1999 | Wollam | |
| 6,071,866 A * | 6/2000 | Fujiwara et al. | 510/130 |
| 6,077,816 A | 6/2000 | Puvvada et al. | |
| 6,429,177 B1 | 8/2002 | Williams et al. | |
| 7,084,104 B2 | 8/2006 | Martin et al. | |
| 7,098,180 B2 | 8/2006 | Ganopolsky et al. | |
| 7,119,059 B2 | 10/2006 | Librizzi et al. | |
| 7,655,607 B2 | 2/2010 | Tsaur et al. | |
| 7,659,235 B2 | 2/2010 | Tsaur et al. | |
| 7,671,000 B2 | 3/2010 | Tsaur et al. | |
| 7,674,759 B2 | 3/2010 | Tsaur | |
| 7,807,612 B2 | 10/2010 | Tsaur | |
| 2004/0224863 A1 | 11/2004 | Sun et al. | |
| 2005/0075256 A1 | 4/2005 | Librizzi et al. | |
| 2005/0100570 A1 | 5/2005 | Wei et al. | |
| 2005/0136026 A1 | 6/2005 | Qiu et al. | |
| 2005/0143268 A1 | 6/2005 | Midha et al. | |
| 2005/0192188 A1 | 9/2005 | Wagner et al. | |
| 2006/0079420 A1 | 4/2006 | Wagner et al. | |
| 2009/0062177 A1 * | 3/2009 | Tsaur | 510/414 |

FOREIGN PATENT DOCUMENTS

| | | |
|---|---|---|
| EP | 0 559 375 A1 | 9/1993 |
| EP | 1029532 | 8/2000 |
| EP | 1 479 365 | 11/2004 |
| EP | 1237534 | 1/2005 |
| GB | 2015561 A | 9/1979 |
| WO | 97/05857 | 2/1997 |
| WO | 99/32069 | 7/1999 |
| WO | 00/21492 | 4/2000 |
| WO | 03/017968 | 3/2003 |
| WO | 2009/077495 A2 | 7/2006 |
| WO | 2008/074617 | 6/2008 |
| WO | 2009/030594 A1 | 3/2009 |

OTHER PUBLICATIONS

PCT Search Report on International Application No. PCT/EP2007/063128 dated Jan. 23, 2009.
PCT Search Report on International Application No. PCT/EP2008/067530 dated Jul. 24, 2009.
PCT Search Report on International Application No. PCT/EP2008/060835 dated Jan. 26, 2009.
PCT Search Report and Written Opinion for International Application No. PCT/EP2009/062278 dated Apr. 16, 2010.
XP-002474464. Oct. 1988, English translation of JP 1987-0077976 (based on JP 63-243200).
Co-pending application for: Applicant: Tsaur et al.; U.S. Appl. No. 12/235955; filed: Sep. 23, 2008: entitled: Stable cleansing compositions containing fatty acyl isethionoate surfactant products having more than 10 wt. % of fatty acid/fatty soap content using high level ot polyol and methods thereof.
Co-pending application for: Tsaur et al.; U.S. Appl. No. 12/751,063, filed Mar. 31, 2010.
Co-pending application for: Tsaur et al.; U.S. Appl. No. 12/751,079, filed Mar. 31, 2010.
Co-pending application for: Tsaur et al.; U.S. Appl. No. 12/577,425, filed Oct. 12, 2009.

* cited by examiner

*Primary Examiner* — Ling Choi
*Assistant Examiner* — Thuy-Al Nguyen
(74) *Attorney, Agent, or Firm* — Ronald A. Koatz

(57) ABSTRACT

The present invention relates to super mild surfactant systems. Specifically, a combination of specific alkanoyls or mixtures of alkanoyl surfactants with specifically identified fatty acyl isethionate product provide synergy which reduces irritation (as measured by Patch Testing) so greatly that it is comparable to mildness which normally can be only achieved using very high amounts of benefit agent (e.g., emollient).

7 Claims, No Drawings

PERSONAL WASH CLEANSER WITH MILD SURFACTANT SYSTEMS COMPRISING DEFINED ALKANOYL COMPOUNDS AND DEFINED FATTY ACYL ISETHIONATE SURFACTANT PRODUCT

FIELD OF THE INVENTION

The present invention relates to novel super mild surfactant compositions for use in personal care cleanser (e.g., personal care liquid body cleansers or shampoos) compositions. Use of these surfactant combinations provides mildness comparable or superior to compositions which provide mildness using very high amounts emollient oils.

BACKGROUND OF THE INVENTION

Personal cleansing compositions which provide cleansing and personal care benefits are known in the art, for example, liquid cleansing market. In order to achieve superior mild and moisturizing skin benefit, very high levels (generally higher than 30% by wt. of liquid compositions) of emollient oils are used in leading marketed moisturizing compositions (e.g., Dove® Cream Oil or Olay® Ribbon body wash compositions).

There has been a continuous effort to provide skin care benefits from personal skin/hair cleanser compositions, for example, by delivering ever increasing amounts of benefit agents such as silicone oil, petrolatum and triglyceride oils from such cleansers. Some products use emollient oils as high as 50% by wt. or more of the composition.

U.S. Pat. No. 5,612,307 to Chambers et al. discloses, for example, use of a single package containing separate stripe of cleansing agents and benefit agents where benefit agent is as high as 50% of the package in order to deliver sufficient benefit agent for efficient skin moisturizing and conditioning. Delivery of benefit requires special packaging, complicated processing and high levels of benefit agent.

U.S. Pat. No. 5,965,500 to Puvvada discloses liquid compositions where the level of emollient exceeds the level of surfactant.

Other references also require very high level of skin benefit agent to deliver skin care benefits (U.S. Publication No. 2005/0100570 A1; U.S. Publication No. 2005/0143268 A1; U.S. Publication No. 2006/0079420 A1, all to Procter & Gamble). The benefit of using very mild surfactant systems to minimize use of benefit agent is not recognized.

Accordingly, there is a need for personal cleanser compositions (e.g., liquid cleansers) which provide superior skin care benefit without requiring use of high levels of benefit agent.

Unpredictably, applicants have found that this aim can be achieved using exceptionally mild surfactant mixtures. It is extremely surprising that the overall level of surfactant can be increased (relative to different systems) while also increasing mildness. Using surfactant systems of the invention, it is possible to achieve significant mildness (as defined in standard Patch Test as disclosed, for example, in Protocol below) while using, for example, much lower levels (e.g., 30% or less) of the types of occlusive emollient oils (e.g., petrolatum, silicone) typically used for providing mildness benefits. Clinical benefits are equal to or better than products tested which comprise, for example, 40% or more petrolatum.

Various other mild cleanser compositions have been claimed. Various references to Johnson & Johnson claim compositions comprising modified acrylic copolymers and common anionic surfactants such as sodium trideceth sulfate (U.S. Pat. No. 7,119,059; U.S. Pat. No. 7,098,180; U.S. Pat. No. 7,084,104; U.S. Publication No. 2005/0075256). U.S. Publication No. 2005/0192188 to Wagner et al. discloses surfactants with a structured domain comprising at least 70% of a lamellar phase made using common surfactant mixtures such as sodium trideceth sulfate and sodium laurylamphoacetate.

Compositions of the subject invention provide unique surfactant systems (using, for example, alkanoyl glycinate and specified fatty acyl isethionate surfactant products), preferably for use in compositions having little to no (e.g., 3% by wt. or less, preferably 2% by wt. or less) alkyl sulfate surfactants (e.g., sodium alkyl sulfate, sodium alkyl ether sulfate), which are common to many cleanser compositions.

BRIEF SUMMARY OF THE INVENTION

More specifically, the personal invention provides novel, super mild personal cleanser (preferably liquid personal cleanser) compositions comprising 1 to 30%, preferably 2 to 25% more preferably 3 to 20% by wt. of a surfactant system comprising:

1) 20 to 85%, preferably 30 to 75% by wt. surfactant system of an alkanoyl surfactant selected from the group consisting of alkanoyl glycinate, alkanoyl sarcosinate and mixtures thereof, wherein the alkyl group on the alkanoyl chain is $C_8$ to $C_{20}$, preferably $C_{12}$ to $C_{16}$ straight chain alkyl (e.g., lauroyl, cocoyl or myristoyl glycinate). Preferably this component comprises at least alkanoyl glycinate although, as noted, alkanoyl sarcosinate alone and mixtures of alkanoyl glycinate and alkanoyl sarcosinate are contemplated. Cocoyl glycinate is a particularly preferred component.

2) 5 to 70% surfactant system of a fatty acyl isethionate product which product comprises 40 to 80% (of the product) fatty acyl isethionate and 15 to 50% (of the product) free fatty acid and/or fatty acid salt/soap (the product may also comprise isethionate salts, typically present at less than 5% of the product and may further comprise traces, e.g., typically less than 2% of product, of other impurities).

In addition, greater than 25% and less than 45% of the fatty acyl isethionate is of chain length (referring to the alkyl chain defining the fatty acyl) of greater than or equal to $C_{16}$; and greater than 50%, preferably greater than 60% of the chain length of free fatty acid and fatty acid soap groups combined are of chain length $C_{16}$ to $C_{20}$. These chain length ranges are important for providing lather and mildness of resulting fatty acyl isethionate product. These critically defined fatty acid isethionate products (which applicants describe in applicants' copending application, U.S. Ser. No. 12/577,425 to Tsaur filed Oct. 12, 2009) and defined alkanoyl surfactants synergistically react to form unique ultra mild surfactant systems of the invention.

Compositions meeting requirements of invention will have irritation score in a Patch Test as % of the same irritation result using 5% solution of sodium dodecyl sulfate (SDS) of less than 90% SDS, preferably 75% or less of SDS score, more preferably 70% or less, more preferably 65% or less and more preferably 60% or less of the SDS irritation score.

In a preferred embodiment of the invention, the compositions comprising the novel mild surfactant system noted above have 3% or less and preferably 2% or less, more preferably 1% or less alkyl sulfate anionic (e.g., sodium dodecyl sulfate or sodium lauryl ether sulfate). In one embodiment, the composition will have substantially no (e.g., 0.2% or less by wt., preferably none whatsoever except for possible impurities) alkyl sulfate anionic.

In another preferred embodiment, surfactant compositions of the invention (comprising 1 to 30% of personal cleanser) will comprise (1) 20 to 85% alkanoyl surfactant; (2) 5 to 70% isethionate product as defined; (3) 20 to 80%, preferably 30 to 70% surfactant system of an amphoteric and/or zwitterionic surfactant (e.g., betaine and/or amphoacetate); and (4) 3% or less, and preferably substantially no, anionic and nonionic surfactant other than (1) and (2) as defined above in the personal cleanser composition (e.g., other than alkanoyl surfactant and isethionate product of (1) and (2)). Even when the amount of total anionic is closer to 3% in this embodiment, most preferably the amount of alkyl sulfate (alkyl sulfate component of the additional anionic) specifically should be minimized as noted in the embodiment above, e.g., it should comprise 1% or less of alkyl sulfate surfactant and, preferably, be absent.

In addition to having any additional anionic and nonionic surfactant be a maximum 3% by wt. of total liquid composition, the anionic and nonionic should be less than 30% of the total amount of glycinate, sarcosinate, isethionate product, amphoteric and zwitterionic in the composition. In other words, 3% of total cleanser composition or 30% of surfactants noted in the immediately preceding sentence, whichever is lower, is the maximum total of anionic and nonionic surfactant present.

These and other aspects, features and advantages will become apparent to those of ordinary skill in the art from a reading of the following detailed description and the appended claims. For the avoidance of doubt, any feature of one aspect of the present invention may be utilized in any other aspect of the invention. It is noted that the examples given in the description below are intended to clarify the invention and are not intended to limit the invention to those examples per se. Other than in the experimental example, or where otherwise indicated, all numbers expressing quantities of ingredients or reaction conditions used herein are to be understood as modified in all instances by the term "about". Similarly, all percentages are weight/weight percentages of the total composition unless otherwise indicated. Numerical ranges expressed in the format "from x to y" are understood to include x and y. When for a specific feature multiple preferred ranges are described in the format "from x to y" it is understood that all ranges combining the different endpoints are also contemplated. Where the term "comprising" is used in the specification or clams, it is not intended to exclude any terms, steps or features not specifically recited. All temperatures are in degrees Celsius (° C.) unless specific otherwise. All measurements are in SI units unless specified otherwise. All documents cited are—in relevant part—incorporated herein by reference.

DETAILED DESCRIPTION OF THE INVENTION

The present invention relates to novel, super mild surfactant compositions used in personal care cleanser compositions such as, for example, liquid cleansers or shampoos. Using the mild surfactant compositions of the invention, it is possible to achieve extremely mild compositions (measured, for example, by standard Patch testing) on par or better than compositions which do not use the same surfactant systems and use significantly higher levels of benefit agent to provide mildness benefit. As such, the invention provides a method for enhancing mildness to obtain composition comparable in mildness to compositions using, for example, 40% or more emollient oil by specific selection of super mild surfactant systems.

The present invention relates to personal care cleanser compositions comprising 1 to 30% by wt., preferably 2 to 25%, more preferably 3 to 20% by wt. of a surfactant system comprising:

1) 20 to 85%, preferably 30 to 75% by wt. of surfactant system of alkanoyl surfactant selected from the group consisting of alkanoyl glycinate, alkanoyl sarconsinate and mixtures thereof wherein alkyl chain on the alkanoyl is $C_8$ to $C_{20}$ alkyl chain;

2) 5 to 70%, preferably 10 to 60% by wt. surfactant system of a fatty acyl isethionate product which product comprises 40 to 80% fatty acyl isethionate and 15 to 50% free fatty acid and/or soap wherein greater than 20% and less than 40% fatty acyl isethionate has chain length greater than or equal to $C_{16}$ and greater than 50% of fatty acid and/or soap has chain length greater than or equal to $C_{16}$ to $C_{24}$.

While mixtures of alkanoyl glycinate and alkanoyl sarcosinate are contemplated, in a preferred form, the compositions comprise alkanoyl glycinate only or at least predominantly (at greater than 50%, preferably greater than 60%, more preferably 75% or greater of the mixture of the glycinate and sarcosinate). Broadly in this embodiment, the ratio of alkanoyl glycinate to alkanol sarcosinate may be from at least 1/3 to 1/0 (e.g., from at least one-quarter of mixture to all glycinate). As noted, preferably the mixture is predominantly alkanoyl glycinate.

In a preferred embodiment discussed below, the compositions have little or substantially no alkyl sulfate. In another embodiment, compositions have little or no anionic and nonionic surfactant at all other than what is present in (1) and (2). Compositions may further preferably comprise amphoteric and/or zwitterionic.

Each of these embodiments is discussed in more detail below, together with other ingredients which may be used in the composition of the invention.

Mild Anionic Surfactant Combination

The first required components of the surfactant system are alkanoyl surfactants which can be alkanoyl glycinates, alkanoyl sarcosinates or mixtures thereof. The alkyl group is $C_8$ to $C_{20}$, preferably $C_{12}$ to $C_{16}$ straight chain alkyl.

Preferred surfactants include cocoyl, lauroyl or myristoyl glycinate and cocoyl, lauroyl or myristoyl sarcosinates. A preferred composition comprises use of only alkanoyl glycinate, e.g., cocoyl glycinate.

A second required component of the mild surfactant system is fatty acyl isethionate product. It was surprising to find that a combination of fatty acyl isethionate product and alkanoyl surfactant(s) lead to enhanced mildness of the cleanser compositions as measured by patch test and LCAT tests described in the protocol section. There is an unexpected synergy between the two.

The preferred fatty acyl isethionate product comprises (in addition to other components) both pure fatty acyl isethionate surfactant (e.g., 40 to 80% of the product) as well as free fatty acid and/or fatty acid salt (e.g., 15 to 50%). In addition, greater than 20%, preferably greater than 25% of the fatty acyl isethionate and less than 45 wt. % are of chain length greater than or equal to $C_{16}$; and greater than 50%, preferably greater than 60% of the free fatty acid/soap is of chain length $C_{16}$ to $C_{20}$.

The fatty acyl isethionate surfactant component is typically prepared by the reaction of an isethionates salt such as alkali metal isethionates and an aliphatic fatty acid having 8 to 20 carbon atoms and Iodine Value (measuring degree of unsaturation) of less than 20 g, for example:

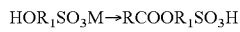

where $R_1$ is an aliphatic hydrocarbon radical containing 2 to 4 carbons;
M is alkali metal cation or metal ion (e.g., sodium, magnesium, potassium, lithium), ammonium or substituted ammonium cation or other counterion; and
R is an aliphatic hydrocarbon radical having 7 to 24, preferably 8 to 22 carbons.

Depending on the processing conditions used, the resulting fatty acyl isethionate product can be a mixture of 40 to 80% by weight of fatty acyl isethionates (which formed from the reaction) and 50 to about 15 wt. %, typically 40 to 20 wt. % of free fatty acids. In addition, product may contain isethionates salts which are present typically at levels less than 5 wt. %, and traces (less than 2 wt. %) of other impurities. Preferably, a mixture of aliphatic fatty acids is used for the preparation of commercial fatty acyl isethionates surfactants. The resulting fatty acyl isethionate surfactants (e.g., resulting from reaction of alkali metal isethionate and aliphatic fatty acid) should have more than 20 wt. %, preferably more than 25%, but no more than 40% wt., preferably 35% (on basis of fatty acyl isethionates reaction product) of fatty acyl group with 16 or greater carbon atoms to provide both lather and mildness of the resulting fatty acyl isethionate product. These longer chain fatty acyl isethionate surfactants and fatty acids, i.e. fatty acyl group and fatty acid with 16 or more carbons, form insoluble surfactant/fatty acid crystals typically in water at ambient temperatures. While not wishing to be bound by theory, it is believed that these long chain fatty acyl isethionate surfactants in the product together with free long chain fatty acids in the product contribute to the mildness of the fatty acyl isethionate product for skin cleanser applications.

Examples of commercial fatty acyl isethionate products that are particularly useful in the subject invention are DEFI flakes and Dove® cleansing bar noodles produced by Unilever. DEFI (Direct Esterification of Fatty Isethionate) flakes typically contain about 68 to 80 wt. % of sodium fatty acyl isethionate and 15 to 30 wt. % free fatty acid. More than 25 wt. % and no more than 35% of fatty acyl group of the resulting fatty acyl isethionate have 16 to 18 carbon atoms. Dove® cleansing bar noodles are mixtures of DEFI flakes described above and long chain (mainly $C_{16}$ and $C_{18}$) fatty acid and fatty soap which contain about 40 to 55 wt. % of fatty acyl isethionate and 30 to 40 wt. % of fatty acid and fatty soap. Due to the high level of long chain (16 or more carbons) fatty acyl isethionate and fatty acid, these preferred fatty acyl isethionate surfactant products are extremely mild and have very good emollient benefits to the skin.

A key aspect of the present invention is that the mild surfactant system selected should be milder than a 0.5% solution of sodium dodecyl sulfate (SDS) measured using the Patch Test method described in the product. Either surfactant mixture of fully formulated liquid composition may be used although fully formulated liquid is preferred. As noted, surfactant system that can be used for the application of this invention should be significantly less irritating to the skin than a 0.5 wt. % SDS solution. According to the definition, the comparison is made using a cumulative irritation score. This is defined in the Patch Test method as having less than 90%, preferably less than 85%, most preferably less than 80% of the cumulative irritation score of the 0.5 wt. % SDS control solution (the higher the score, the more irritating). Surfactant systems that meet the mildness criteria are found to cause less damage to the skin during the use of a product. This makes it possible to deliver superior skin repair and conditioning benefits without the need of incorporating extremely high level of emollient oils as required in current leading skin care body washes as shown in the examples disclosed in this invention. Liquid cleanser compositions that meet the criteria described above deliver similar to or better than a high petrolatum-containing (greater than 45 wt. %) commercial moisturizing body wash, e.g., Olay® Butter Ribbon, using 30 wt. %, or even as low as 10 wt. % of petrolatum.

In order to ensure that this level of mildness is achieved, it is required that there be no more than a maximum amount of certain specific anionics; or maximum amount of combined anionic and nonionic surfactant (other than components (1) and (2)) present in the composition of the invention.

In particular, the compositions preferably have 3% or less, preferably 2% or less, more preferably 1% or less of any alkyl sulfate anionic including alkyl sulfates such as sodium dodecyl sulfates or alkoxylated sulfates such as lauryl ether sulfate. In a preferred embodiment, the compositions will have 0.2% or less anionic surfactant and, in particular 0.2% or less alkyl sulfate.

In another preferred embodiment, the compositions will comprise (1) 20 to 85% of surfactant system alkanoyl surfactant; (2) 5 to 70% of surfactant system isethionate product as defined above, (3) 20 to 80%, preferably 30 to 70% of surfactant system amphoteric and zwitterionic surfactant; and (4) 3% or less anionic and nonionic altogether (other than what is found in (1) and (2)) in the cleanser composition.

Another way to define substantial absence of anionic and nonionic surfactant is that the sum of the two must comprise 30% or less of total amount of glycinate, sarcosinate, isethionate product, amphoteric and zwitterionic present. Total anionic and nonionic is therefore 3% or less of total composition, or 30% or less of total surfactants noted in previous sentence, whichever is lower.

While the amount of surfactant used is constrained as noted above, examples of surfactants which can be used are noted below.

The anionic surfactant may be, for example, an aliphatic sulfonates, such as a primary alkane (e.g., $C_8$-$C_{22}$) sulfonates, primary alkane (e.g., $C_8$-$C_{22}$) disulfonate, $C_8$-$C_{22}$ alkene sulfonate, $C_8$-$C_{22}$ hydroxyalkane sulfonate or alkyl glyceryl ether sulfonate (AGS); or an aromatic sulfonate such as alkyl benzene sulfonate.

The anionic may also be an alkyl sulfate (e.g., $C_{12}$-$C_{18}$ alkyl sulfate) or alkyl ether sulfate (including alkyl glyceryl ether sulfates). Among the alkyl ether sulfates are those having the formula:

wherein R is an alkyl or alkenyl having 8 to 18 carbons, preferably 12 to 18 carbons, n has an average value of greater than at least 0.5, preferably between 2 and 3; and M is a solubilizing cation such as sodium, potassium, ammonium or substituted ammonium.

The anionic may also be alkyl sulfosuccinates (including mono- and dialkyl, e.g., $C_6$-$C_{22}$ sulfosuccinates); fatty acyl taurates, fatty acyl amino acids other than lauroyl and cocoyl glycinate or sarcosinate, alkyl sulfoacetates, $C_8$-$C_{22}$ alkyl phosphates, alkyl phosphate esters and alkoxyl alkyl phosphate esters, acyl lactates, $C_8$-$C_{22}$ monoalkyl succinates and maleates, and fatty acyl isethionates.

Another class of anionics is carboxylates such as follows:

wherein R is $C_8$ to $C_{20}$ alkyl; n is 0 to 10; and M is as defined above.

Another carboxylate which can be used is amido alkyl polypeptide carboxylates such as, for example, Monteine LCQ® by Seppic.

The nonionic surfactants which may be used include in particular the reaction products of compounds having a hydrophobic group and a reactive hydrogen atom, for example aliphatic alcohols, acids, amides or alkyl phenols with alkylene oxides, especially ethylene oxide either alone or with propylene oxide. Specific nonionic detergent compounds are alkyl ($C_6$-$C_{22}$) phenols-ethylene oxide condensates, the condensation products of aliphatic ($C_8$-$C_{18}$) primary or secondary linear or branched alcohols with ethylene oxide, and products made by condensation of ethylene oxide with the reaction products of propylene oxide and ethylenediamine. Other so-called nonionic detergent compounds include long chain tertiary amine oxides, long chain tertiary phosphine oxides and dialkyl sulphoxides.

The nonionic may also be a sugar amide, such as a polysaccharide amide. Specifically, the surfactant may be one of the lactobionamides described in U.S. Pat. No. 5,389,279 to Au et al. which is hereby incorporated by reference or it may be one of the sugar amides described in U.S. Pat. No. 5,009,814 to Kelkenberg, hereby incorporated into the subject application by reference.

Preferred alkyl polysaccharides are alkylpolyglycosides of the formula:

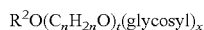

$$R^2O(C_nH_{2n}O)_t(glycosyl)_x$$

wherein $R^2$ is selected from the group consisting of alkyl, alkylphenyl, hydroxyalkyl, hydroxyalkylphenyl, and mixtures thereof in which alkyl groups contain from about 10 to about 18, preferably from about 12 to about 14, carbon atoms; n is 0 to 3, preferably 2; t is form 0 to about 10, preferably 0; and x is from 1.3 to about 10, preferably from 1.3 to about 2.7. The glycosyl is preferably derived from glucose.

The zwitterionic and amphoteric surfactants which are used in preferred embodiments of the invention are as noted below.

Zwitterionic surfactants are exemplified by those which can be broadly described as derivatives of aliphatic quaternary ammonium, phosphonium, and sulfonium compounds, in which the aliphatic radicals can be straight or branched chain, and wherein one of the aliphatic substituents contains from about 8 to about 18 carbon atoms and one contains an anionic group, e.g., carboxy, sulfonate, sulfate, phosphate, or phosphonate. A general formula for these compounds is:

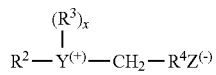

$$R^2-Y^{(+)}(R^3)_x-CH_2-R^4Z^{(-)}$$

wherein $R^2$ contains an alkyl, alkenyl, or hydroxyl alkyl radical of from about 8 to about 18 carbon atoms, from 0 to about 10 ethylene oxide moieties and from 0 to about 1 glyceryl moiety; Y is selected from the group consisting of nitrogen, phosphorus, and sulfur atoms; $R^3$ is an alkyl or monohydroxyalkyl group containing about 1 to about 3 carbon atoms; X is 1 when Y is a sulfur atom, and 2 when Y is a nitrogen or phosphorus atom; $R^4$ is an alkylene or hydroxyalkylene of from about 1 to about 4 carbon atoms and Z is a radical selected from the group consisting of carboxylate, sulfonate, sulfate, phosphonate, and phosphate groups.

Examples of such surfactants include:
4-[N,N-di(2-hydroxyethyl)-N-octadecylammonio]-butane-1-carboxylate;
5-[S-3-hydroxypropyl-5-hexadecylsulfonio]-3-hydroxypentane-1-sulfate;
3-[P,P-diethyl-P-3,6,9-trioxatetradexocylphosphonio]-2-hydroxypropane-1-phosphate;

Amphoteric surfactants which may be used in this invention include at least one acid group. This may be a carboxylic or a sulphonic acid group. They include quaternary nitrogen and therefore are quaternary amido acids. They should generally include an alkyl or alkenyl group of 7 to 18 carbon atoms. They will usually comply with an overall structural formula:

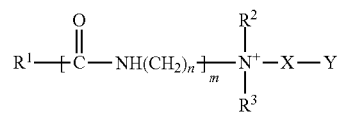

$$R^1-\overset{O}{\overset{\|}{C}}-NH(CH_2)_n\overset{}{\underset{m}{-}}\overset{R^2}{\underset{R^3}{N^+}}-X-Y$$

where $R^1$ is alkyl or alkenyl of 7 to 18 carbon atoms;
$R^2$ and $R^3$ are each independently alkyl, hydroxyalkyl or carboxyalkyl of 1 to 3 carbon atoms;
n is 2 to 4;
m is 0 to 1;
X is alkylene of 1 to 3 carbon atoms optionally substituted with hydroxyl, and
Y is 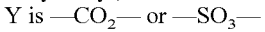 —$CO_2$— or —$SO_3$—

Alkylamphoacetates and dialkylamphoacetates are also intended to be covered among possible amphoteric compounds which may be used.

Examples of suitable amphoteric surfactants are alkyl betaines; amidoalkyl betaines; amphocarboxylate derivatives such as (mono or di) alkylamphoacetate; and amidoalkyl sultains.

Cocamidopropybetaine, lauramidopropyl betaine, lauryl betaine, cocobetaine, lauroamphoacetate, cocoamphoacetate, cocoamphopropionate, lauryl hydroxysultaine and cocamidopropyl hydroxysultaine surfactants are particularly useful and preferred for this application.

In another embodiment of the invention, the compositions seek to deliver skin or hair benefit agent (in particular petrolatum for skin and silicone oil for hair, for example) in the mild surfactant compositions of the invention (to ensure low mildness scores measured, for example, by Patch Test) through use of small skin or hair benefit agent particles in combination with cationic polymer combined with minimizing use of lauric acid. This is described below.

There are at least two possible ways to deliver skin or hair benefit agent onto the skin or hair during the use of the products. One is through the interaction of small skin or hair benefit agent particles with cationic polymers. In this case the skin or hair benefit agent particles in the liquid composition should be in the range of 0.01 to 30 micrometers. Upon dilution of the liquid composition with water at 50 times or more, i.e., during use of the liquid product, these small particles interact with cationic polymers to form aggregates of benefit agent/polymer flocs with aggregate length of 10 up to several hundreds micrometers. Cationic polymer such as modified polysaccharides including cationic guar available from Rhone Poulenc under the trade name Jaguar® C13S, Jaguar® C14S, Jaguar® C17, or Jaguar® C16; BF® Guar C17 from Lamberti, Aqua D4091® or Aqua D4051® from Aqualon; cationic modified cellulose such as UCARE Polymer JR 30® or JR 40® from Amerco are useful for this application. Formation of benefit agent/polymer aggregates with length from 10 to several hundreds micrometers upon dilution with water is critical for efficient delivery of benefit agent onto the skin. Applicants found that the benefit agent/polymer floc formation is sensitive to the liquid composition containing fatty acyl isethionate surfactant product of our invention, especially to the level of extra lauric acid added into the liquid. To ensure efficient delivery of benefit agent using cationic polymer as deposition aid, the amount of lauric acid added to the liquid for better liquid properties (such as viscosity and lather) should be minimized. In general, extra lauric acid added into liquids of this invention using cationic polymer as deposition aid for skin or hair benefit agent (e.g., emollient oil) should be no more than 3.0 wt. %, preferably no more than 2.5 wt. %, most preferably no more than 2.0 wt. %.

Another way to deliver skin or hair benefit agent is through the direct contact of the dispersed skin or hair benefit agent (e.g., droplets) with skin or hair during the use of the product. In this case, the skin or hair benefit agent droplet size has to be larger than 50 micrometers up to several thousand micrometers and the benefit agent droplet should be viscous with viscosity more than 5,000 centipoises such as petrolatum or thickened low viscosity oil as taught in U.S. Pat. No. 5,804,540.

A preferred skin or hair benefit agent for the application of this invention for skin is petrolatum and for hair is silicone. The total amount of skin or hair benefit agent in the composition of this invention can be 1 to 60 wt. %, preferably 2 to 50 wt. %, more preferably 3 to 35 wt. %.

Other nutrients and moisturizers are noted below.

One class of ingredients is nutrients used to moisturize and strengthen, for example, the skin. These include:
  (a) vitamins such as vitamin A and E, and vitamin alkyl esters such as vitamin C alkyl esters;
  (b) lipids such as cholesterol, cholesterol esters, lanolin, sucrose esters, and pseudo-ceramides;
  (c) liposome forming materials such as phospholipids, and suitable amphophilic molecules having two long hydrocarbon chains;
  (d) essential fatty acids, poly unsaturated fatty acids, and sources of these materials;
  (e) triglycerides of unsaturated fatty acids such as sunflower oil, primrose oil, avocado oil, almond oil;
  (f) vegetable butters formed from mixtures of saturated and unsaturated fatty acids such as Shea butter;
  (g) minerals such as sources of zinc, magnesium, and iron.

A second type of skin benefit agent is a skin conditioner used to provide a moisturized feel to the skin. Suitable skin conditioners include:
  (a) silicone oils, gums and modifications thereof such as linear and cyclic polydimethylsiloxanes, amino, alkyl, and alkyl aryl silicone oils;
  (b) conditioning proteins such as milk proteins, silk proteins and glutens;
  (c) emollients such as esters of long chain fatty acids, such as isopropyl palmitate and cetyl lactate.

A third type of benefit agent is deep cleansing agents. These are defined here as ingredients that can either increase the sense of refreshment immediately after cleansing or can provide a sustained effect on skin problems that are associated with incomplete cleansing. Deep cleansing agents include:
  (a) antimicrobials such as 2-hydroxy-,2',4'-trichlorodiphenylether (DP300), 2,6-dimethyl-4-hydroxychlorobenzene (PCMX), 3,4,4'-trichlorocarbanilide (TCC), 3-trifluoromethyl-4,4'-dichlorocarbanilide (TFC), benzoyl peroxide, zinc salts, tea tree oil;
  (b) anti-acne agents such as salicylic acid, lactic acid, glycolic acid, and citric acid, and benzoyl peroxide (also an antimicrobial agent);
  (c) oil control agents including sebum suppressants, modifiers such as silica, titanium dioxide, oil absorbers, such as micro sponges;
  (d) astringents including tannins, zinc and aluminum salts, plant extracts such as from green tea and Witch-hazel (Hammailes),
  (e) scrub and exfoliating particles, such as polyethylene spheres, agglomerated silica, sugar, ground pits, seeds, and husks such as from walnuts, peach, avocado, and oats, salts;
  (f) cooling agents such as methanol and its various derivatives and lower alcohols;
  (g) fruit and herbal extracts;
  (h) skin calming agents such as aloe vera
  (i) essential oils such as jasmine, camphor, white cedar, bitter orange peel, rye, turpentine, cinnamon, bergamot, citrus unshiu, calamus, pine, lavender, bay, clove, hiba, eucalyptus, lemon, starflower, thyme, peppermint, rose, sage, menthol, cineole, sugenol, citral, citronelle, borneol, linalool, geranoil, evening primrose, camphor, tymol, spirantol, penene, limonene and terpenoid oils.

Other benefit agents that can be employed include anti-dandruff compounds such as zinc pyrithione for shampoo application, anti-aging compounds, sunscreens, and lightening agents.

When the benefit agent is oil, especially low viscosity oil, it may be advantageous to pre-thicken it to enhance its delivery. In such case, hydrophobic polymers of the type describe in U.S. Pat. No. 5,804,540 (which is incorporated by reference into the subject application) may be used.

Water Soluble Skin Benefit Agents

Water-soluble skin benefit agents is another optional ingredient that is highly preferred to be include in the liquid compositions of the invention. A variety of water-soluble skin benefit agents can be used and the level can be from 0 to 50 weight %, preferably 1 to 30%. The materials include, but are not limited to, polyhydroxy alcohols such as glycerin, propylene glycol, dipropylene glycol, sorbitol, pantenol and sugar; urea, alpha-hydroxy acid and its salt such as glycolic or lactic acid; and low molecular weight polyethylene glycols with molecular weight less than 20,000. Preferred water soluble skin benefit agents for use in the liquid composition are glycerin and diglycerin.

Water soluble/dispersible polymers are an optional ingredient that is preferred to be included in the liquid composition of the invention. The water soluble/or dispersible polymer can be cationic, anionic, amphoteric or nonionic polymer with molecular weight higher than 100,000 Dalton. These polymers are known to increase the viscosity and stability of liquid cleanser compositions, to enhance in-use and after-use skin sensory feels, and to enhance lather creaminess and lather stability. When water insoluble skin benefit agent is used in this invention, the water soluble/dispersible polymers are required to stably suspend the added skin benefit agents. Amount of polymers used can be in the range of 0.1 up to 10 wt. % depending on the composition of the liquid cleansers.

Examples of water soluble/or dispersible polymers useful in the present invention include the carbohydrate gums such as cellulose gum, microcrystalline cellulose, cellulose gel, hydroxethyl cellulose, hydroxypropyl cellulose, sodium carboxymethylcellulose, hydroxymethyl or carboxymethyl cellulose, methyl cellulose, ethyl cellulose, guar gum, gum karaya, gum tragacanth, gum Arabic, gum acacia, gum agar, xanthan gum and mixtures thereof; modified and non-modified starch granules with gelatinization temperature between 30 to 85° C. and pregelatinzed cold water soluble starch; polyacrylate; Carbopols; alkaline soluble emulsion polymer such as Aculyn 28, Aculyn 22 or Carbopol Aqua SF1; cationic polymer such as modified polysaccharides including cationic guar available from Rhone Poulenc under the trade name Jaguar C13S, Jaguar C14S, Jaguar C17, or Jaguar C16; BF Guar C17 from Lamberti, Aqua D4091 or Aqua D4051 from Aqualon; cationic modified cellulose such as UCARE Polymer JR 30 or JR 40 from Amerchol; N-Hance 3000, N-Hance 3196, N-Hance GPX215 or N-Hance GPX 196 from Hercules; synthetic cationic polymer such as MerQuat 100, MerQuat 280, Merquat 281 and Merquat 550 by Nalco; cationic starches, e.g., StaLok® 100, 200, 300 and 400 made by Staley Inc.; cationic galactomannans based on guar gum of Galactasol 800 series by Henkel, Inc.; Quadrisect Um-200; and Polyquaternium-24.

Gel forming polymers such as modified or non-modified starch granules, xanthan gum, Carbopol, alkaline-soluble emulsion polymers and cationic guar gum such as Lamberti BF Guar C17, and cationic modified cellulose such as UCARE Polymer JR 30® or JR 40® are particularly preferred for this invention.

As discussed in copending application relating to benefit agent delivery through floc formation, when such delivery is used, anionic polymer (e.g., Carbopol®) should be preferably minimized to reduce formulation costs.

Other Optional Components

In addition, the compositions of the invention may include 1 to 10% by wt. optional ingredients as follows:

Perfumes; sequestering agents, such as tetra sodium ethylenediaminetetraacetate (EDTA), EHDP or mixtures in an amount of 0.01 to 1%, preferably 0.01 to 0.05%; and coloring agents, opacifiers and pearlizers such as zinc striate, magnesium stearate, $TiO_2$, EGMS (ethylene glycol monostearate) or Lytron 621 (Styrene/Acrylate copolymer); all of which are useful in enhancing the appearance or cosmetic properties of the product.

The compositions may further comprise antimicrobials such as 2-hydroxy-4,2'4'trichlorodiphenyl ether (DP300); preservatives such as dimethyloldimethylhydantoin (Glydant XL 1000), parabens, sorbic acid, etc.

Antioxidants such as, for example, butylated hydroxytoluene (BHT) may be used advantageously in amounts of about 0.01% or higher if appropriate.

Polyethylene glycols as conditioners which may be used include:

| | | |
|---|---|---|
| Polyox | WSR-25 | PEG 14M |
| Polyox | WSR-N-60K | PEG 45M, or |
| Polyox | WSR-N-750 | PEG 7M. |

Another ingredient which may be included are exfoliants such as polyoxyethylene beads, walnut shells and apricot seeds.

EXAMPLES

Protocol

Patch Test

This was randomized, double-blind study. A sufficient number of subjects were recruited to ensure that 25 subjects completed the study. The 14-day cumulative irritation test was conducted as follows. Patching occurred for 14 consecutive days, except on Sundays. Patches applied on Saturday were left in place until Monday, when freshly prepared patches were applied. The designated patch test sites were approximately 2 cm×2 cm on the intrascapular area of the back. Approximately 0.2 mL of the test product was placed onto a Parke-Davis Readi-Bandage® occlusive patch that measured 2 cm×2 cm. Solutions were made by diluting the cleansers to 25% w/w in distilled water. The patch was then applied to the designated test site. The patches were secured with hypoallergenic tape (Scanpor {Allerderm} as needed). A 0.5% sodium dodecyl sulfate (SDS) solution was used as the control in the test.

Each day following application, the patches were removed, the sites evaluated and identical patches reapplied to the same test sites. All evaluations were made using the following 6-point scoring system:

0=No evidence of any effect
+=Barely perceptible (minimal, faint, uniform or spotty erythema) numerically equivalent to 0.5
1=Mild (pink, uniform erythema covering most of the contact site)
2=Moderate (pink-red, erythema uniform in the entire contact site)
3=Marked (bright red erythema with/without petechiae or papules)
4=Severe (deep red erythema with/without vesiculation or weeping)

If a dermal reaction of 3 or 4 occur with any of the test articles at any point during the study, further patch testing on that subject was terminated at the test site involved, and the attained score was assigned to that site for the subsequent scheduled test days.

Cumulative irritation scores, which were the sum of the numerical irritation grades assigned daily during the 14-day test period, were calculated at the end of the study to compare mildness of the test products. Based on the 26 subjects completing the study, the highest "Cumulative Irritation Score" that could be obtained was 1456 (26 subjects×14 days×4 [0-4 scoring scale]). The data were statistically analyzed using Tukey-Kramer Comparison, and statistical significance was determined at the 95% confidence level.

LCAT (Leg Controlled Application Technique)

LCAT clinical study was a randomized, double blind incomplete block design with subjects 18-65 years of age (n=49) and was conducted according to Standard Protocol #HPC CAT2004 Hill Top-Controlled Application Technique for Estimating the Relative Mildness of Personal Cleansing Products. The study consisted of a five-day conditioning phase followed by either a five-day or a seven-day product application phase. Qualified subjects completed the five-day in-home conditioning phase using unscented Dove bar according to their normal wash regime. During the conditioning phase, subjects discontinued use of all moisturizers, lotions, sunscreens, and washing appliances on or near their lower legs. Subjects having dryness scores between 1.5-3.5 and erythema scores of <2.0 at the end of the conditioning phase continued into five-day product application phase.

Each outer lower leg was divided and marked with a skin-marking pen into three 3 cm diameter test sited, for a total of 6 test sites. Product application consisted of two wash sessions per day, morning and afternoon at least 3-hour apart, for days 1 to 4 or 1 to 6, and one wash session at morning on the fifth or seventh day respectively for five day or seven day product application study. Each wash session consisted of two washes performed in succession. During product application, study personnel dispersed 0.2 ml of the designated liquid cleanser onto a moistened Masslinn towel and squeezed slightly to generate lather. All test sites were washed for 10 seconds, followed by a 90 second lather retention, 15 seconds rinse with warm water, and then patted dry with a Masslinn towel.

Visual evaluation of dryness and erythema were conducted three times daily (before washed 1 and 3 and 2 hours after wash 4) and twice on last day of the product application phase (before wash 1 and before final instrument readings). Instrumental ServoMed was used to measure transepidermal water loss (TEWL) done at baseline (Day 1 before wash 1) and endpoint (3 to 5 hours after the last wash session on either Day 5 or Day 7 or when a test site was discontinued form further product application). Skicon for the measurement of conductance and Corneometer for capacitance reading were done twice daily (before wash 1 at A.M., and 2 hours after wash 4 at P.M.) and at baseline and endpoint (3 to 5 hours after the last wash session on either Day 5 or Day 7 or when a test site was discontinued from further product application). Subject continued using unscented Dove® bar (formulation noted below) for all general bathing, excluding the lower legs and continued not using moisturizers, lotions, sunscreens, or washing appliances throughout the product application phase.

Unscented Dove® ingredient listing: sodium cocoyl isethionate, stearic acid, sodium tallowate; or sodium palmitate, sodium stearate, water, sodium isethionate, lauric acid, sodium $C_{14}$-$C_{16}$ olefin sulfonate, sodium cocoate or sodium palm kernalate; sodium chloride, maltol, dipropylene glycol, tetrasodium EDTA, tetrasodium etidronate, titanium dioxide.

Example 1

In order to demonstrate that there is a need to make milder cleanser formulations (e.g., liquid cleansers) without using very large amounts of, for example, petrolatum and mineral oil, applicants compared patch test results of three (3) leading commercial skin care body washes as set forth in Table 1 below. The table ingredients and brief comments are set forth below.

TABLE 1

Patch Test Score of leading commercial skin care body wash liquids

| Composition Tested | 0.5% SDS Solution | Dove Deep Moisture Body Wash | Olay Ultra Moisture Body Wash | Olay butter Ribbon Body Wash |
|---|---|---|---|---|
| Patch test Total irritation score | 783 | — | 987 | 970 |
| Total irritation score compared to 0.5% SDS solution | 100% | — | 126% | 123% |
| Patch test Total irritation score | 912 | 1023 | — | — |
| Total irritation score compared to 0.5% SDS solution | 100% | 112% | — | — |
| % oil | — | 13% | Not available | >45% |

Three leading commercial skin care liquid cleansers—i.e. Dove Deep Moisture Body Wash (ingredient list: water, sunflower seed oil, sodium laureth sulfate, cocamidopropyl betaine, glycerin, petrolatum, lauric acid, cocamide MEA, fragrance, santalum album oil, guar hydroxypropyltrimonium chloride, lanolin alcohol, PEG-30 dipolyhydroxystearate, DMDM hydantoin, EDTA, citric acid, etidronic acid, $TiO_2$); Olay® ultra moisture body wash (ingredient list: water, petrolatum, ammonium laureth sulfate, ammonium lauryl sulfate, sodium lauroamphoacetate, lauric acid, fragrance, trihydroxystearin, sodium chloride, guar hydroxypropyltrimonium chloride, citric acid, DMDM hydatoin, sodium benzoate, EDTA, niaciamide, PEG-14M, butyrospermum parki extract, tocopheryl acetate, retinyl palmitate; and Olay® Butter ribbons body wash (ingredient list: water, petrolatum, mineral oil, sodium trideceth sulfate, sodium lauryl sulfate, sodium lauroamphoacetate, sodium chloride, trideceth-3, fragrance, simmondsia chinensis (Jojoba) butter, citric acid, guar hydroxypropyltrimonium chloride, acrylonitrile/methacrylonitrile/methylmethacrylate copolymer, isopentane, xanthan gum, sodium benzoate, PEG-90M, disodium EDTA, methylchloro isothiazolinone, methylisothiazolinone, sodium hydroxide, Red 7, Green 6) were evaluated in patch test compared to the standard 0.5% SDS (Na dodecyl sulfate) solution. The results are summarized in Table 1.

As shown in the table, the total irritation score for all three leading commercial skin care body washes is higher than the 0.5% SDS solution. To achieve superior moisturizing benefit, very high level of emollient oils, such as Olay Butter ribbon containing more than 45% petrolatum and mineral oil, are used in these products.

The results clearly show that there is a need to make milder liquid as defined in this invention, for skin care liquid cleanser application to achieve superior skin cleansing and skin moisturizing benefit without the need of using very high level of emollient oils as current leading commercial skin care body washes. The examples of this invention noted below show that liquid cleanser compositions containing the super mild surfactant system as defined in this invention, having significantly lower level of petrolatum, can achieve similar or better skin care benefit, as shown in clinical studies, than even a leading commercial body wash containing more than 45% of emollient oils (Olay® Butter Ribbon).

Examples 2-5 and Comparatives A-F

The examples in the table below were prepared for mildness comparison using the Patch Test method. All the examples were prepared by mixing all the ingredients except perfume and glydant plus at 70 to 75° C. for 30 to 40 minutes to form a uniform mixture. Perfume and glydant plus were added below 40° C. The pH of the samples was adjusted with NaOH or citric acid solution to the range of 6.4 to 7.0 at the end of preparation.

Table 2 is set forth below:

| | Example No. | | | | | | | | |
|---|---|---|---|---|---|---|---|---|---|
| | 2 | | | 3 | 4 | 5 | | | |
| | | | | Comparative example | | | | | |
| | A | B | C | | | | D | E | F |
| Cocoamidopropylbetaine | 5 | 5 | 5.5 | — | — | 4.8 | 4.8 | 5 | 4.5 | 3.5 |
| Na lauryl amphoacetate | — | — | — | 2.5 | 2.5 | — | — | — | — | — |

-continued

| | Example No. | | | | | | | | |
|---|---|---|---|---|---|---|---|---|---|
| | 2 | | | 3 | 4 | 5 | | | |
| | | | | Comparative example | | | | | |
| | A | B | C | | | | D | E | F |
| Na lauryl 1EO sulfate | — | — | 4.5 | — | — | — | — | 5 | 5.5 | 6.8 |
| K cocoyl glycinate | 5 | 5 | — | 2.5 | 2.5 | — | — | — | — | — |
| Na cocoyl glycinate | — | — | — | — | — | 2.5 | 2.5 | — | — | — |
| Na lauroyl sarcosinate | — | — | — | — | — | 2.5 | 2.5 | — | — | — |
| Na cocoyl isethionate (Joranpon CI) | — | 2 | — | — | — | — | — | — | 2 | — |
| Na fatty acyl isethionate product | — | 10 | 12 | — | 4 | 4 | 2 | — | 10 | 12 |
| Lauric acid | 1 | — | 2.5 | 0.6 | 0.6 | 2.4 | 2.4 | 1 | — | 3.0 |
| Jaguar C13S | 0.1 | 0.3 | 0.3 | 0.05 | — | — | — | 0.1 | 0.3 | 0.3 |
| Jaguar C17 | — | — | — | — | 0.2 | — | — | — | — | — |
| Lamberty BF17 | — | — | — | — | — | 0.5 | 0.5 | — | — | — |
| Pure Gel B990 Starch | 7 | — | — | 5 | 5 | 6 | 6 | — | — | — |
| Glycerin | 30 | 30 | 5 | 10 | 10 | 6 | 6 | 30 | 30 | 5 |
| Petrolatum | 20 | 20 | 6 | 20 | 20 | 30 | 30 | 20 | 20 | 6 |
| Soybean oil | — | — | — | — | — | — | — | — | — | — |
| Glydant plus | 0.2 | 0.2 | 0.2 | 0.2 | 0.2 | 0.2 | 0.2 | 0.2 | 0.2 | 0.2 |
| Perfume | 1 | 1 | 1 | 0.6 | 0.6 | 1 | 1 | 1 | 1 | 1 |
| Total irritation score as % of 0.5% SDS solution | 92.3% | 70.0% | 87.6% | 83.6% | 50.4% | 40.1% | 49.2% | 104% | 91.6% | 99.6% |

The total irritation score as percentage compared to 0.5% SDS solution for each sample is also given in Table 2. Lower percentage of total cumulative irritation score (by percentage) indicates milder surfactant system. As shown in the table, Comparative Examples D, E and F containing high level of sodium alkyl ether sulfates, mild synthetic surfactants widely claimed in mild liquid cleanser patents and which are most widely used in current commercial mild personal care liquid cleansers, all have very high total irritation score with numbers higher or almost same as the 0.5% SDS solution even for the liquid (Comparative Example D), containing 50 wt. % of NaLES and 50 wt. % amphoteric surfactant (cocamidopropyl betaine). To make mild liquid composition with cumulative irritation score significantly lower than 0.5% SDS solution (defined as less than 90% of 0.5% SDS total irritation score), alkyl ether sulfates level has to be reduced (see Comparative B relative to Comparative F where reduction went from 99.6% to 87.6% score) or removed altogether (see Comparative C versus D, E and F).

A surprising and unpredictable finding is that the combination of a fatty acyl isethionate surfactant product to the liquid composition can enhance the mildness of other synthetic surfactant (e.g., alkanoyl surfactants) when levels of anionic and nonionic are minimized. This specific fatty acyl isethionate product contain about 50 wt. % of fatty acyl isethionate surfactant with about 30% of the fatty acyl group equal to or longer than 16 carbon, and about 35 wt. % of linear fatty acid/linear fatty soap in which about 79 wt. % of the fatty acid/fatty soap have 16 to 20 carbons. This is seen, for example, in comparing Comparative A (no isethionate product) to Example 2 and Comparative C to Example 3.

It was unexpected that addition of any extra surfactants, which might be examples to introduce irritation (fatty acyl isethionate surfactant product), can enhance mildness of other synthetic surfactants.

The combination of this fatty acyl isethionate product with alkanoyl surfactant(s) defined, however, provides synergy to lower the irritation of liquid cleanser.

Examples 6-8 and Comparatives G-J

In order to further show benefits of the invention, applicants conducted LCAT clinical tests for compositions set forth in the table below:

TABLE 3

| | Example No. | | | | | | |
|---|---|---|---|---|---|---|---|
| | | 6 | | 7 | 8 | | |
| | | | | Comparative example | | | |
| | G | — | H | — | — | I | J |
| Na fatty acyl isethionate product HEBE noodle | — | 10 | — | 4 | 4 | — | — |
| Na cocoyl isethionate | — | 2 | — | — | — | — | — |
| Na cocoamidopropyl betaine | 5 | 5 | 4.4 | 4.4 | 4.8 | 5 | 2 |
| Na lauryl amphoacetate | — | — | — | — | — | — | — |
| K cocoyl glycinate | 5 | 5 | — | — | — | — | — |
| Na cocoyl glycinate | — | — | 4.6 | 4.6 | 2.5 | — | — |
| Na laurath (1EO) sulfate | — | — | — | — | — | 5 | — |
| Na laurath (3EO) sulfate | — | — | — | — | — | — | 9 |
| Na lauryol sarcosinate | — | — | — | — | 2.5 | — | 3 |
| Cocomonoethanolamide | — | — | — | — | — | — | 1 |
| Lauric acid | 1 | 0 | 0.8 | 0.6 | 1.8 | 1 | 2.5 |
| Cationic guar Jaguar C13S | 0.1 | 0.3 | 0.4 | 0.5 | — | 0.1 | 0.35 |
| Cationic guar Lamberti cosmetic BF7 | — | — | — | — | 0.5 | — | — |
| Glycerin | 30 | 30 | 10 | 10 | 6 | 30 | — |
| Petrolatum | 18 | 20 | 30 | 30 | 10 | 18 | 40 |
| Penreco Snow White Indopol H1500 polybutene | 2 | — | — | — | 2 | 2 | — |
| Indopol H300 polybutene | — | — | — | — | — | — | 3 |
| Pure gel B990 starch | 7 | — | 6.5 | 5 | 6 | 7 | — |
| Perfume | 1 | 1 | 1 | 1 | 1 | 1 | 1 |

TABLE 3-continued

| | Example No. | | | | | | |
|---|---|---|---|---|---|---|---|
| | 6 | | 7 | 8 | | | |
| | | | | Comparative example | | | |
| | G | — | H | — | — | I | J |
| LCAT clinical results | | | | | | | |
| TEWL | >R | >R | = | >R | = | = | >R |
| Conductance | = | >R | >R | >R | >R | = | = |
| Visual dryness | = | >R | >R | >R | = | = | = |
| CAPACITANCE | >R | >R | >R | >R | = | = | = |
| ERYTHEMA | >R | >R | >R | >R | = | >R | = |

Seven samples with composition shown in Table 3 were prepared using the same procedure as described above for LCAT (Leg Controlled Application Technique) clinical study. The LCAT clinical results conducted according to the method disclosed in this patent are also summarized in Table 3. In the LCAT study, Olay Butter Ribbon Body Wash containing more than 45% petrolatum is used as the control for comparison. A "=" sign indicates there is no significant difference between the test sample and the Olay Ribbon Butter. A ">R" means the test sample is significantly better than Olay butter Ribbon in that clinical measurement. If the test sample is significantly worse than Olay Butter Ribbon, "<R" will be shown in that specific clinical measurement.

Several interesting observations may be made from the results in the Table.

From Comparative I and J, it can be seen the compositions containing anionic (alkoxylated sulfate) have typical parity with Olay® (which has more than 45% petrolatum). From Comparative G, it can be seen that removal of this anionic alone improves clinical results. Examples 6 and 7 clearly show that combination of isethionate product and defined alkanoyl provide clinical superiority. While Comparative H (using glycinate and no alkoxylated sulfate) shows superiority, it is noted that, at equal levels of petrolatum, Example 7 is even superior. Example 8 shows that, even at levels of 10% petrolatum, the surfactant system of the invention provided mildness at par or perhaps slightly better than the formulation with more than 45% petrolatum. This is a truly unpredictable achievement.

Examples 9-10

TABLE 4

| | Example No. | |
|---|---|---|
| | 9 | 10 |
| Na fatty acyl isethionate product noodle | 1 | 4 |
| Na cocoamidopropyl betaine | 6 | 6 |
| Na cocoyl glycinate | 4 | 4 |
| Na lauryol sarcosinate | 1 | 1 |
| Lauric acid | 1.6 | 0.8 |
| Cationic guar | 0.2 | 0.2 |

TABLE 4-continued

| | Example No. | |
|---|---|---|
| | 9 | 10 |
| DC1788 silicon oil emulsion | 3 | 3 |
| DC7123K silicon oil emulsion | 1.67 | 1.67 |
| Zinc pyrithione | 2.08 | 2.08 |
| Pure gel B990 starch | 8 | 8 |
| Glydant plus | 0.1 | 0.1 |
| EDTA* | 0.077 | 0.077 |
| Methyl paraben | 0.2 | 0.2 |
| Perfume | 0.8 | 0.8 |

*ethylenediaminetetraacetc acid

Examples 9 and 10 with composition shown in Table 4 were prepared for anti-dandruff shampoo application.

What is claimed is:

1. A liquid cleansing composition comprising:
   (1) 1 to 30% by wt. of a surfactant system comprising:
      (a) 30 to 70% by wt of surfactant system of a mixture of alkanoyl glycinate and alkanoyl sarcosinate wherein the ratio of said alkanoyl glycinate to alkanoyl sarcosinate is of from 1/0 to 1/3 and the alkyl group on the alkanoyl chain is C8 to C20;
      (b) 10 to 60% by weight of surfactant system of a fatty acyl isethionate product which product comprises 40 to 80% fatty acyl isethionate and 15 to 50% free fatty acid and/or fatty acid salt, and
      (c) 20 to 80% by weight of surfactant system of amphoteric and/or zwitterionic surfactant;
   wherein greater than 25% and less than 45% of the fatty acyl isethionate is of chain length C16 or greater; and greater than 50% of chain length of free fatty acid and fatty acid salt groups combined are of chain length $C_{16}$ to $C_{20}$
   wherein the composition comprises 3% or less of an alkyl sulfate anionic surfactant; and
   wherein total irritation score using Patch Test Methodology is less than 75% relative to a 0.5% solution of sodium dodecyl sulfate used as control in the same Patch Test.

2. A composition according to claim 1 comprising 2 to 20% by wt. of said surfactant system comprising components (a), (b) and (c).

3. A composition according to claim 1 that comprises 3% or less of any anionic and nonionic surfactants other than alkanoyl surfactant and isethionate product of (a) and (b).

4. A composition according to claim 3 further comprising 1% or less alkyl sulfate.

5. A composition according to claim 3 comprising 2% or less anionic and nonionic surfactant.

6. A composition according to claim 3 comprising substantially no anionic or nonionic surfactant.

7. A composition according to claim 1 in which anionic or nonionic surfactant comprises less than 30% of total glycinate, sarcosinate, isethionate product and amphoteric and zwitterionic found in the composition.

* * * * *